United States Patent [19]

Cross et al.

[11] 3,932,167

[45] Jan. 13, 1976

[54] SUBSTITUTED S-TRIAZINES AS HERBICIDAL AGENTS

[75] Inventors: Barrington Cross, Rocky Hill; Richard William Feeny, Hightstown, both of N.J.

[73] Assignee: American Cyanamid Company, Stamford, Conn.

[22] Filed: Oct. 26, 1973

[21] Appl. No.: 409,841

Related U.S. Application Data

[62] Division of Ser. No. 301,561, Oct. 27, 1972, Pat. No. 3,816,419.

[52] U.S. Cl. .................................................... 71/93
[51] Int. Cl.² ......................................... A01N 9/22
[58] Field of Search ........................................ 71/93

[56] References Cited

UNITED STATES PATENTS

| | | | |
|---|---|---|---|
| 2,891,855 | 6/1959 | Gysin et al. | 71/93 |
| 2,909,420 | 10/1959 | Gysin et al. | 71/93 |
| 3,086,855 | 4/1963 | Knusli et al. | 71/93 |
| 3,753,986 | 8/1973 | Singhal et al. | 71/93 |

OTHER PUBLICATIONS

Chem. Abst. Vol. 72 (1970) 132679z.

Primary Examiner—Lewis Gotts
Assistant Examiner—Catherine L. Mills
Attorney, Agent, or Firm—H. G. Jackson

[57] ABSTRACT

This invention relates to the use of substituted s-triazine compounds as herbicides.

9 Claims, No Drawings

3,932,167

SUBSTITUTED S-TRIAZINES AS HERBICIDAL AGENTS

This is a division of application Ser. No. 301,561, filed Oct. 27, 1972, now U.S. Pat. No. 3,816,419.

BACKGROUND OF THE INVENTION

1. Field of the Invention

The invention pertains to chemicals for herbicidal use.

2. Description of the Prior Art

S-triazines are well known as herbicidal agents. One disclosure in the patent literature of s-triazines containing haloalkyl groups is claimed by Geigy British Pat. No. 922,587, (1963) (U.S. Pat. No. 3,086,855, 1963). Further some of the compounds in our invention are described in a paper by Shapiro, Parrino and Feedman, *Journal of Organic Chemistry* 25, p. 379, (1960) and a method of preparation of certain amino substituted perfluoroalkyl-s-triazines by J. T. Shaw and F. J. Gross, *Journal of Organic Chemistry* 24, 1809, (1959), and a patent to American Cyanamid Company by J. T. Shaw, U.S. Pat. No. 3,305,390 (1963), relating to the preparation of some of these compounds.

Our invention, however, is the first to describe herbicidal haloalkyl s-triazines containing cycloalkylamino or aralkylamino substituents and it describes the advantageous activity and uses of these compounds.

SUMMARY OF THE INVENTION

This invention is novel s-triazine compounds of the formula:

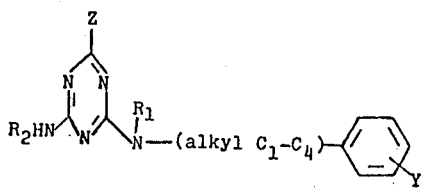

where Z is haloalkyl $C_1$–$C_3$ or haloalkenyl $C_1$–$C_3$ containing from 1 to 5 halogen atoms; $R_1$ and $R_2$ each represent hydrogen, alkyl $C_1$–$C_4$ or cyanoalkyl wherein the alkyl group contains 1 to 4 carbon atoms; Y is hydrogen, halogen, alkyl $C_1$–$C_2$, nitro, cyano, alkoxy $C_1$–$C_2$, haloalkyl $C_1$–$C_2$ or alkyl $S(O)_n$, and n is an integer 0, 1 or 2. The invention includes a method for controlling undesirable plant species with s-triazine compounds of the formula:

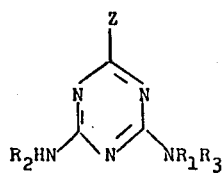

wherein $R_1$, $R_2$, Y, Z and $n$ are as described above and $R_3$ is cycloalkyl $C_3$–$C_7$ optionally substituted with methyl or ethyl,

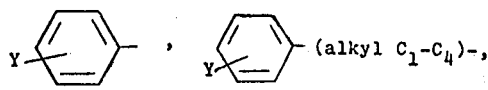

furyl, tetrahydrofurfuryl, pyridyl or heteroalkyl, wherein the hetero ring is furyl, tetrahydrofuryl or pyridyl and the alkyl group contains 1 to 4 carbon atoms.

DETAILED DESCRIPTION

In accordance with this invention s-triazine compounds having the structure:

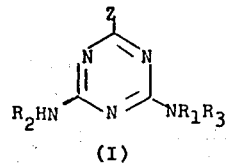

wherein $R_1$, $R_2$, $R_3$ and Z are as described above, can be prepared by suspending or dissolving an appropriately substituted biguanide (II) or its salt (HX) in a solvent such as ethanol, methanol, n-propanol, methoxyethanol, ethoxyethanol or the like. If the HX salt is used, sufficient base such as sodium methoxide, potassium t-butoxide or the like is added to neutralize the HX group. It is also advantageous to add up to one additional mole of base in order to increase the rate of s-triazine formation for the less reactive substituted biguanides (II). The neutralized biguanide solution is then treated with a lower alkyl ester of a haloalkylcarboxylic acid or haloalkenylcarboxylic acid. The reaction generally proceeds satisfactorily at a temperature between about 10° and 50°C., however, in some instances the mixture may be heated to about 100°C. to improve the reaction rate. The reaction mixture is then poured into an ice and water mixture and the solid s-triazine product filtered off and crystallized. This reaction may be graphically illustrated as follows:

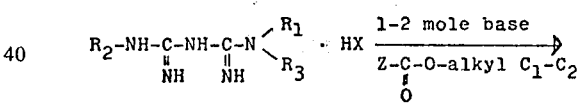

(II)

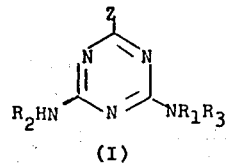

(I)

As used in this application the terms "halo" and "halogen", unless otherwise defined, mean chlorine, fluorine, bromine and iodine.

Preferred new compounds of the invention are of the formula:

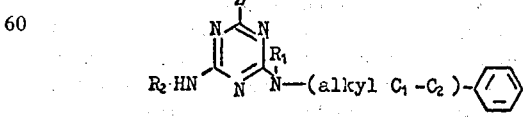

wherein Z is haloalkyl $C_1$–$C_2$, and $R_1$ and $R_2$ each represent hydrogen or methyl.

Although trichloromethyl s-triazines (I, Z = $CCl_3$) can be prepared in very poor yields by the procedure described above, we have found that these compounds can be prepared by an alternative process characterized by a marked improvement in product yield. This process involves the treatment of tris-2,4,6-trichloromethyl-s-triazine with one mole of an amine having the structure: $HNR_1R_3$ where $R_1$ and $R_3$ are as described above. The reaction is generally carried out at a temperature between about 10° and 50°C. in a lower alcohol such as methanol in the presence of a tertiary amine such as triethylamine. This reaction yields the intermediate monoamino-s-triazine (III) which is further reacted with an amine having the structure: $NH_2R_2$ where $R_2$ is as described above. The latter reaction is preferably carried out under conditions similar to those described for preparation of the intermediate monoamino-s-triazine (III) and produces the trichloromethyl-s-triazine (I, $Z = CCl_3$). The reaction may be illustrated as follows:

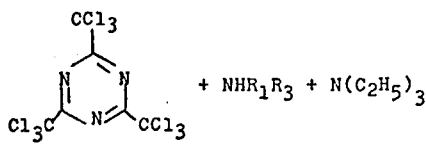

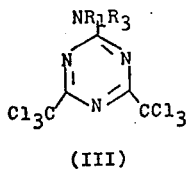

(III)

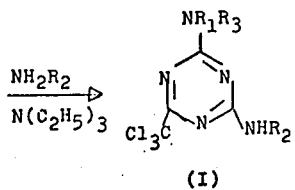

(I)

Although the intermediate biguanides (II) herein described are well known compounds aralkyl and cycloalkylbiguanides were only inconveniently and inefficiently produced by fusion reactions between dicyanamide and the appropriate aralkylamine hydrochloride or cycloalkylamine hydrochloride. Additionally, cycloalkylbiguanides have been prepared from the fusion of guanyl isoureas and amines, or the fusion of cyanoguanidines with ammonium sulfonates. A reaction between biguanides and arylamines in the presence of copper sulfate and a solvent such as alcohol has also been reported and preparation of cyclohexylbiguanide by this method is indicated.

Of these above procedures, dicyanamide and alkylamine hydrochlorides afford the most convenient starting materials. Unfortunately, only arylamine salts are reported to react with dicyanamide in solvents below 100° and fusion reactions are necessary for reaction to proceed for cycloalkylamines and aralkylamine salts in the temperature range 130°–165°C. We now find that cycloalkyl and aralkylbiguanide salts may be prepared almost quantitatively by conducting the above reactions in the temperature range 120°–200°C. and preferably between 140° and 150° in a high boiling solvent of preferably low dielectric constant. Thus, a preferred solvent is o-dichlorobenzene. Highest yields are attained by efficient stirring of the reaction mixture. A reaction time in the range of 0.5 hour to 3 days is usually sufficient. The biguanide hydrochloride thus precipitates out and on cooling the reaction may be filtered off in almost quantitative yield, in analytical purity. This procedure offers considerable advantages over the previous art, due to increased yield (quantitative), due to ease of operation of a liquid phase reaction rather than a hazardous fusion, due to the easy removal and isolation of the precipitated biguanide salt by filtration. The reaction may be illustrated as follows:

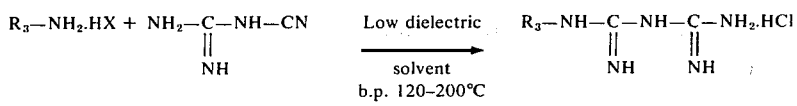

$R_3$ = cycloalkyl; $R_3$ = aralkyl.

The compounds of this invention are useful as herbicidal agents. They exhibit a high degree of postemergence activity against a wide variety of undesirable monocotylendonous and dicotylendonous plants and can be applied with conventional type applicators in solid or liquid formulations. The compounds of the invention are also highly effective preemergence herbicides and can be effectively used for the selective control of undesirable broadleaf weeds and grasses in the presence of agronomic crops such as corn, cotton, soybeans and rice. Moreover, the compounds of the invention may be used alone or in combination with other pesticides, including other herbicides, fungicides, insecticides, bactericides and acaricides.

Among the solid formulations which can be prepared are dusts, dust concentrates, wettable powders and granular formulations.

Dusts are usually prepared by grinding together from about 1% to 15% by weight of the substituted s-triazine and about 99% to 85% by weight of an inert carrier such as attapulgite, kaolin, diatomaceous earth, talc, silica or the like. The dusts may also be prepared by dissolving the s-triazine in acetone or similar solvent and spraying the thus prepared solution on the carrier.

Dust concentrates are prepared in the same manner as dusts excepting that about 16% to 85% by weight of the substituted s-triazine is used.

Wettable powders are made up in the same way dust concentrates are prepared; however, about 1% to 10% by weight of a surface active agent is usually added. Where desired about 1% to 5% of a dispersant may also be added to the formulation.

Among the surfactants which may be used in the above-mentioned formulations are naphthalene sulfonic acid condensate, polyoxyethylated vegetable oil alkylphenoxypolyoxyethylene ethanol, mono and diglycerides of fatty acids and alkali metal alkylnaphthalene sulfonates.

Sodium lignin sulfonate and the calcium salt of a polymerized alkyl aryl sulfonic acid are typical of the dispersants which can be used in the wettable powder formulations.

Granular formulations can be prepared on either sorptive or nonsorptive carriers. With sorptive carriers such as particulate attapulgite, activated carbon, corn cob grits or the like, the active compound can be dissolved in a solvent such as acetone, methyl ethyl ketone or methanol, and the solution sprayed on an agitated or tumbling bed of particulate material. When nonsorptive carriers such as granular limestone, sand or coconut shell is used, the carrier is usually treated with a binder solution such as a solution of sodium lignin sulfonate or sugar solution and coated with the active material applied either alone or as a dust or dust concentrate.

In practice, the active compounds are generally applied as the formulated products in sufficient amount to provide about 0.06 to 10 pounds of active ingredient per acre of treated area. At the higher rates of application (e.g. about 4.0 to 10 lbs. per acre) excellent control of a very wide variety of broadleaf weeds and grasses is generally achieved. However, where selective pre or postemergence control of undesirable broadleaf weeds and grasses is sought, the active compound is usually applied at about 0.06 to 4.0 pounds per acre depending upon the undesirable plant species involved and/or the crop which may be present.

The invention is further illustrated by the examples set forth below.

EXAMPLE 1

Preparation of 2-Amino-4-cyclohexylamino-6-(trifluoromethyl)-s-triazine

To a suspension of N-cyclohexylbiguanide hydrochloride (600 g., 2.73 mole) in methanol (37 l.) is added at 54° powdered sodium methoxide (294 g., 5.44 mole) followed by methyl trifluoroacetate (350 g., 2.74 mole) dropwise with stirring over 1.5 hours. The addition is exothermic and the reaction temperature rises to 65° during the addition. The reaction is stirred at 60° for 16 hours and poured into ice-water to give a precipitate that is filtered off, water washed and air dried to give a white powder, 520 g., 73%, m.p. 164°–7°. Crystallization of a small sample from acetonitrile gives the product m.p. 167°–8°.

The s-triazines in Table I are prepared by this procedure employing the appropriate substituted biguanide II and haloalkylcarboxylic acid ester.

Following the above procedure and substituting N-(2-methylcyclohexyl)biguanide hydrochloride or N-(2-ethylcyclohexyl)biguanide hydrochloride for the above biguanide yields 2-amino-4-(2-methylcyclohexyl)amino-6-(trifluoromethyl)-s-triazine and 2-amino-4-(2-ethylcyclohexyl)amino-6-trifluoromethyl)-s-triazine, respectively.

TABLE I

Preparation of s-triazines by the biguanide route as in Example 1 by the equation

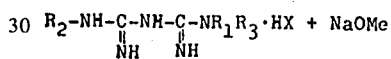

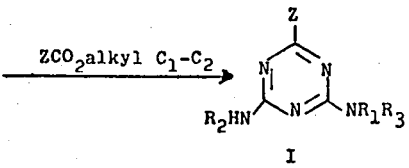

| Z | $R_2$ | $R_1$ | $R_3$ | m.p.(°C) | Calc. | Anal. (%) Found |
|---|---|---|---|---|---|---|
| —$CF_3$ | H | H | $C_6H_5$ | 185–186 | | |
| —$CF_3$ | H | H | $C_6H_{11}$ | 167–8 | | |
| —$CF_3$ | H | H | —⟨C₆H₄⟩—Cl | 186.5–187 | C 41.49<br>H 2.43<br>N 24.17<br>F 19.67<br>Cl 12.24 | C 41.45<br>H 2.29<br>N 24.23<br>F 19.30<br>Cl 12.32 |
| —$CF_3$ | —$C(CH_3)_3$ | H | —⟨C₆H₄⟩—Cl | 102–103 | C 48.63<br>H 4.37<br>N 20.26<br>Cl 10.25<br>F 16.48 | C 48.87<br>H 4.23<br>N 20.11<br>Cl 10.13<br>F 16.69 |
| —CHClF | H | H | —$C_6H_5$ | 152–155 | N 27.62 | N 27.48 |
| —$CCl F_2$ | H | H | —$C_6H_5$ | 184–185 | C 44.26<br>H 2.97<br>N 25.79<br>F 13.99<br>Cl 13.05 | C 44.50<br>H 2.84<br>N 25.85<br>F 13.69<br>Cl 13.25 |
| —$CHF_2$ | H | H | —$C_6H_5$ | 157–158 | C 50.63<br>H 3.82<br>N 29.53 | C 51.22<br>H 3.62<br>N 29.90 |
| —$CF_3$ | —$CH(CH_3)_2$ | H | —⟨C₆H₄⟩—Cl | 135–136 | C 47.08<br>H 3.95<br>N 21.12<br>F 17.19 | C 47.14<br>H 3.99<br>N 21.05<br>F 16.93 |

-continued

| Z | R₂ | R₁ | R₃ | m.p.(°C) | Calc. Anal. (%) | Found |
|---|---|---|---|---|---|---|
| | | | | | Cl 10.69 | Cl 10.91 |
| —CF₃ | H | H | ⟨phenyl-CH₃⟩ | 180.5–181.5 | C 49.10<br>H 3.70<br>N 26.00<br>F 21.17 | C 49.12<br>H 3.76<br>N 25.97<br>F 21.33 |
| —CF₃ | H—CH(CH₃)₂ | | —C₆H₅ | 164–165 | C 52.86<br>H 4.10<br>N 23.72<br>F 19.31 | C 52.47<br>H 4.79<br>N 23.64<br>F 19.25 |
| —CF₂—CF₃ | H | H | —C₆H₅ | 187–188 | | |
| —CF₃ | H | CH₃ | —C₆H₅ | 147–147.5 | C 49.10<br>H 3.70<br>N 26.00<br>F 21.17 | C 49.31<br>H 3.86<br>N 26.11<br>F 20.94 |
| —CHCl₂ | H | H | ⟨cyclohexyl⟩ | 119.5–120 | C 43.48<br>H 5.47<br>N 25.36<br>Cl 25.67 | C 43.72<br>H 5.43<br>N 25.44<br>Cl 25.63 |
| —CClF₂ | H | H | ⟨cyclohexyl⟩ | 153–154 | C 43.24<br>H 5.68<br>N 25.23<br>Cl 12.76 | C 43.73<br>H 5.16<br>N 25.63<br>Cl 12.79 |
| —CHF₂ | H | H | ⟨cyclohexyl⟩ | 151–151.5 | C 49.37<br>H 6.22<br>N 28.79 | C 49.77<br>H 6.11<br>N 29.00 |
| —CHFCl | H | H | ⟨cyclohexyl⟩ | 139.5–140 | C 46.24<br>H 5.82<br>N 26.98<br>Cl 13.66 | C 46.97<br>H 5.90<br>N 27.05<br>Cl 13.55 |
| —C₂F₅ | H | H | ⟨cyclohexyl⟩ | 127–128 | C 42.41<br>N 22.49 | C 42.76<br>N 22.32 |
| —CHClCH₃ | H | H | ⟨cyclohexyl⟩ | 127–128.5 | C 51.52<br>H 7.09<br>N 27.38<br>Cl 13.87 | C 51.95<br>H 7.66<br>N 26.45<br>Cl 13.37 |
| —CFCl₂ | H | H | ⟨cyclohexyl⟩ | 140–141 | C 40.83<br>H 4.80<br>N 23.81 | C 40.92<br>H 4.68<br>N 23.50 |
| —CHBr₂ | H | H | ⟨cyclohexyl⟩ | 150–151 | C 32.89<br>H 4.14<br>N 19.19 | C 33.82<br>H 4.23<br>N 18.89 |

EXAMPLE 2

Preparation of 2-Amino-4-benzylamino-6-(trifluoromethyl)-s-triazine

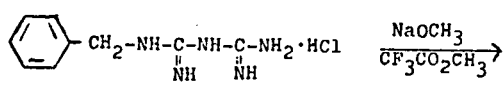

To benzylbiguanide hydrochloride (11.3 g., 0.05 mole) in methanol (270 ml.) is added powdered sodium methoxide (5.4 g., 0.1 mole) followed by methyl trifluoroacetate (6.4 g., 0.05 mole) dropwise with stirring. The solution is stirred at room temperature for 64 hours, then poured into ice-water (500 ml.) and a white solid precipitated and is filtered off, m.p. 183°–185°C. Crystallization from acetonitrile affords colorless cubic crystals, m.p. 184°–185°C. Yield 8 g. (60%)

TABLE II

Preparation of aralkylamino-s-triazines by the route as in Example 2 by the equation

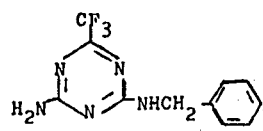 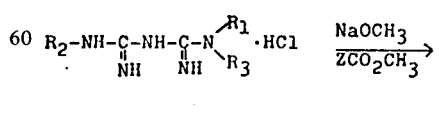

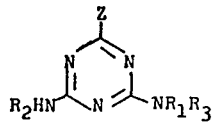

| Z | $R_2$ | $R_1$ | $R_3$ | m.p.(°C) | Anal. Calc. (%) | Found |
|---|---|---|---|---|---|---|
| —$CF_3$ | H | H | —$CH_2$—Ph | 184–185 | C 49.26<br>H 3.38<br>N 26.12<br>F 21.25 | C 48.76<br>H 3.58<br>N 26.01<br>F 21.85 |
| —$CF_3$ | H | H | —$CHCH_3$—Ph | 127–128 | C 50.87<br>H 4.27<br>N 24.73<br>F 20.12 | C 50.86<br>H 4.15<br>N 24.88<br>F 20.23 |
| —$CF_2$—$CF_3$ | H | H | —$CH_2$—Ph | 100.5–101 | C 45.14<br>H 3.16<br>N 21.95<br>F 29.77 | C 45.37<br>H 3.42<br>N 21.59<br>F 29.51 |
| —$CClF_2$ | H | H | —$CH_2$—Ph | 135–136 | C 46.24<br>H 3.53<br>N 24.52<br>F 13.30<br>Cl 12.41 | C 46.54<br>H 3.70<br>N 24.60<br>F 13.19<br>Cl 12.30 |
| —$CHCl_2$ | H | H | —$CH_2$—Ph | 150–150.5 | C 46.66<br>H 3.56<br>N 24.74<br>Cl 25.04 | C 46.88<br>H 3.80<br>N 24.43<br>Cl 24.48 |
| —$CH_2Cl$ | H | H | —$CH_2$—Ph | 135–136 | C 52.90<br>H 4.85<br>N 28.05<br>Cl 14.20 | C 53.24<br>H 5.01<br>N 27.74<br>Cl 14.00 |
| —$CHClCH_3$ | H | H | —$CH_2$—Ph | 126–127 | C 54.66<br>H 5.35<br>N 26.57 | C 55.8<br>H 5.7<br>N 26.46 |

EXAMPLE 3

Preparation of 2-Benzylamino-4,6-bis-trichloromethyl-s-triazine

Benzylamine (3.21 g., 0.03 mole) is added to 2,4,6-tris(trichloromethyl)-s-triazine (13 g., 0.03 mole) in dry benzene (75 ml.). Triethylamine (3.24 g., 0.03 mole) is then added to the reaction mixture and the solution set aside for 3 days. Evaporation to a residual oil and crystallization from methanol-water (9:1) gives the product 10.7 g., 85%, m.p. 96.5°–97°.

Anal.: Calc'd. for $C_{12}H_8N_4Cl_6$: C, 34.25; H, 1.92; N, 13.31; Cl, 50.54. Found: C, 34.10; H, 1.92; N, 13.40; Cl, 50.61.

EXAMPLE 4

Preparation of 2-Amino-4-benzylamino-6-(trichloromethyl)-s-triazine

To a solution of 2-benzylamino-4,6-bis-trichloromethyl-s-triazine (3.15 g., 0.0075 mole) in methanol (70 ml.) is added concentrated ammonium hydroxide (10 ml.) and the temperature raised to 60° for 0.5 hour, cooled and the solvent removed under reduced pressure to give a solid. Crystallization from methanol gives the product, m.p. 210°–212°.

Anal.: Calc'd. for $C_{11}H_{10}N_5Cl_3$: C, 42.43; H, 3.16. Found: C, 43.33; H, 2.82%.

In a similar manner, substituting aqueous methylamine for ammonia, 2-benzylamino-4-methylamino-6-(trichloromethyl)-s-triazine m.p. 86°–87° was prepared.

Anal.: Calc'd. for $C_{12}H_{12}N_5Cl_3$: C, 43.33; H, 3.64. Found: C, 43.08; H, 3.60%.

EXAMPLE 5

The postemergence herbicidal activity of the compounds of the present invention is demonstrated by the following tests, wherein a variety of monocotyledonous and dicotyledonous plants are treated with test compounds dispersed in aqueous acetone mixtures. In the tests, seedling plants are grown in 2 inch square plastic pots for about two weeks. The test compounds are dispersed in 50/50 acetone/water mixtures containing 0.5% surfactant in sufficient quantity to provide the equivalent of about 0.06 to 10 pounds per acre of active compound when applied to the plants through a spray nozzle operating at 40 psi. for a pre-determined time. After spraying, the plants are placed on greenhouse benches and are cared for in the usual manner, commensurate with conventional greenhouse practices. Two weeks after treatment, the seedling plants are examined and rated according to the rating system provided below. The data obtained are reported in the Table below where it can be seen that the test compounds are highly effective for the control of undesirable broadleaf weeds and grasses.

Plant Abbreviations:
- LA — Lambsquarters
- MU — Mustard
- PI — Pigweed
- RAG — Ragweed
- MG — Morningglory
- BA — Barnyard grass
- CR — Crabgrass
- GRF — Green foxtail
- WO — Wild oats
- COR — Corn
- COT — Cotton SOY — Soybean
SB — Sugar beets
RI — Rice Rating System:

| | | % Difference in Growth from the Check* |
|---|---|---|
| 0 | — no effect | 0 |
| 1 | — possible effect | 1 – 10 |
| 2 | — slight effect | 11 – 25 |

| | | |
|---|---|---|
| 3 | — moderate effect | 26 – 40 |
| 5 | — definite injury | 41 – 60 |
| 6 | — herbicidal effect | 6 – 75 |
| 7 | — good herbicidal effect | 76 – 90 |
| 8 | — approaching complete kill | 91 – 99 |
| 9 | — complete kill | 100 |
| 4 | — abnormal growth, i.e. a definite physiological malformation but with an overall effect less than a 5 on the rating scale. | |

*Based on visual determination of stand, size, vigor, chlorosis, growth malformation and overall plant appearance.

TABLE III

Postemergence Herbicidal Activity

| Structure | Treatment lb./Acre | Annual Weeds | | | | | | | | | Crops | | | | |
|---|---|---|---|---|---|---|---|---|---|---|---|---|---|---|---|
| | | LA | MU | PI | RAG | MG | BA | CR | GRF | WO | COR | COT | SOY | SB | RI |
| $F_3C$-triazine-NH-phenyl ($NH_2$) | 9 | 9 | 9 | 9 | 9 | | 8 | 8 | 9 | 3 | 9 | 3 | 8 | 9 | |
| | 3 | 9 | 9 | 9 | 9 | | 8 | 5 | 8 | 3 | 9 | 8 | 8 | 9 | |
| | 1 | 9 | 9 | 7 | 9 | | 8 | 3 | 8 | 5 | 9 | 8 | 9 | 9 | |
| | 0.5 | 9 | 9 | 7 | 6 | | 3 | 2 | 2 | 2 | 3 | 3 | 8 | 9 | |
| $F_3C$-triazine-NH-cyclohexyl | 9 | 9 | 9 | 9 | 9 | | 9 | 9 | 9 | 9 | 9 | 9 | 9 | 9 | |
| | 3 | 9 | 9 | 8 | 9 | | 9 | 9 | 9 | 9 | 9 | 9 | 9 | 9 | |
| | 1 | 9 | 9 | 9 | 9 | | 9 | 7 | 9 | 8 | 9 | 9 | 9 | 9 | |
| | .25 | 8 | 9 | 9 | 9 | | 2 | 6 | 8 | 3 | 8 | 9 | 9 | 9 | |
| $F_3C$-triazine-NH-phenyl-Cl | 9 | 9 | 9 | 9 | 9 | | 9 | 7 | 9 | 3 | 9 | 9 | 9 | 9 | |
| | 3 | 9 | 9 | 9 | 9 | | 8 | 7 | 9 | 2 | 9 | 9 | 8 | 9 | |
| | 1 | 9 | 9 | 9 | 9 | | 6 | 6 | 9 | 2 | 7 | 9 | 9 | 9 | |
| | 0.5 | 9 | 9 | 9 | 8 | | 7 | 2 | 7 | 1 | 9 | 8 | 7 | 9 | |
| $CF_3$-triazine-NH-$CH_2$-phenyl | 9 | 9 | 9 | 9 | 9 | | 9 | 9 | 9 | 8 | 9 | 9 | 9 | 9 | |
| | 3 | 9 | 9 | 9 | 9 | 9 | 9 | 9 | 9 | 9 | 9 | 9 | 9 | 9 | |
| | .25 | 8 | 9 | 9 | 9 | | 8 | 7 | 9 | 7 | 9 | 9 | 9 | 9 | |
| | .13 | 8 | 9 | 9 | 9 | | 3 | 5 | 9 | 3 | 9 | 9 | 9 | 9 | |
| $F_3C-F_2C$-triazine-NH-phenyl | 4 | 9 | 9 | 7 | 9 | | 3 | 8 | 7 | 2 | 9 | 5 | 8 | 8 | |
| | 1 | 8 | 9 | 2 | 7 | | 7 | 3 | 5 | 2 | 2 | 2 | 7 | 8 | |
| | 0.5 | 2 | 9 | 1 | 1 | | 2 | 5 | 3 | 1 | 9 | 2 | 5 | 3 | |
| | .25 | 1 | 9 | 0 | 1 | | 0 | 1 | 1 | 0 | 2 | 1 | 1 | 2 | |
| $CF_3$-triazine-NH-phenyl-$CH_3$ | 1 | 5 | 9 | 2 | 3 | | 1 | 2 | 2 | 1 | 2 | 1 | 3 | 5 | |
| | 0.5 | 1 | 1 | 1 | 0 | | 0 | 0 | 1 | 0 | 7 | 3 | 1 | 2 | |
| $ClF_2C$-triazine-NH-phenyl | 4 | 8 | 9 | 9 | 9 | | 8 | 7 | 6 | 1 | 2 | 9 | 8 | 9 | |
| | 1 | 9 | 9 | 9 | 9 | | 2 | 3 | 8 | 2 | 7 | 9 | 5 | 9 | |
| | 0.5 | 2 | 9 | 8 | 6 | | 3 | 2 | 2 | 2 | 9 | 5 | 5 | 7 | |
| | .25 | 2 | 7 | 2 | 3 | | 1 | 1 | 1 | 1 | 1 | 3 | 2 | 3 | |
| $F_2CH$-triazine-NH-phenyl | 4 | 8 | 9 | 8 | 5 | | 5 | 1 | 5 | 3 | 7 | 9 | 6 | 3 | |
| | 1 | 1 | 3 | 2 | 1 | | 1 | 1 | 1 | 1 | 2 | 5 | 3 | 1 | |
| | 0.5 | 1 | 1 | 1 | 0 | | 0 | 0 | 0 | 0 | 1 | 3 | 2 | 1 | |
| $F_3C$-triazine-NH-phenyl/NHCH($CH_3$)$_2$ | 4 | 9 | 9 | 9 | 9 | | 6 | 5 | 9 | 8 | 9 | 9 | 8 | 9 | |
| | 1 | 9 | 9 | 9 | 6 | | 6 | 2 | 9 | 7 | 9 | 7 | 8 | 9 | |
| | 0.5 | 7 | 9 | 9 | 6 | | 5 | 1 | 7 | 1 | 8 | 6 | 5 | 9 | |

TABLE III-continued
Postemergence Herbicidal Activity

| Structure | Treatment lb./Acre | Annual Weeds | | | | | | | | | Crops | | | | |
|---|---|---|---|---|---|---|---|---|---|---|---|---|---|---|---|
| | | LA | MU | PI | RAG | MG | BA | CR | GRF | WO | COR | COT | SOY | SB | RI |
| | .25 | 8 | 9 | 9 | 7 | | 5 | 1 | 7 | 1 | 7 | 6 | 5 | 9 | |
| F$_3$C—, NH$_2$, NH—CH(CH$_3$)—Ph | 4 | 9 | 9 | 9 | 9 | | 9 | 9 | 9 | 9 | 9 | 9 | 9 | 9 | |
| | 1 | 9 | 9 | 9 | 9 | | 9 | 9 | 9 | 9 | 9 | 9 | 9 | 9 | |
| | .25 | 9 | 9 | 9 | 9 | | 6 | 5 | 9 | 8 | 9 | 9 | 9 | 9 | |
| | .13 | 9 | 9 | 9 | 9 | | 5 | 5 | 7 | 3 | 9 | 9 | 9 | 9 | |
| F$_3$C—CF$_2$—, NH$_2$, NH—CH$_2$—Ph | 10 | 9 | 9 | 9 | 9 | 8 | 3 | 7 | 2 | 8 | | | | | |
| | 4 | 9 | 9 | 9 | 9 | 9 | 9 | 9 | 9 | 9 | 9 | 9 | 9 | | |
| | 1 | 9 | 9 | 9 | 9 | 9 | 8 | 8 | 7 | 9 | 7 | 6 | 9 | | |
| | 0.5 | 9 | 9 | 9 | 9 | 9 | 3 | 7 | 2 | 8 | 5 | 5 | 3 | | |
| F$_2$ClC—, NH$_2$, NH—CH$_2$—Ph | 10 | 9 | 9 | 9 | 9 | 8 | 7 | 7 | 9 | 6 | | | | | |
| | 4 | 9 | 9 | 9 | 9 | 9 | 9 | 9 | 9 | 9 | 9 | 9 | 9 | | |
| | 1 | 9 | 9 | 9 | 9 | 9 | 9 | 8 | 7 | 5 | 9 | 9 | 9 | | |
| | 0.5 | 9 | 9 | 9 | 9 | 9 | 5 | 5 | 3 | 3 | 9 | 3 | 9 | | |
| Cl$_3$C—, NHCH$_3$, NH—CH$_2$—Ph | 1 | 9 | 9 | 9 | 9 | 9 | 5 | 3 | 5 | 9 | 7 | 5 | 9 | | |
| | .25 | 9 | 9 | 9 | 5 | 9 | 2 | 1 | 3 | 8 | 9 | 8 | 8 | | |
| | .13 | 9 | 9 | 9 | 5 | 1 | 1 | 1 | 2 | 7 | 1 | 2 | 2 | | |
| | .06 | 9 | 9 | 9 | 0 | 1 | 1 | 1 | 1 | 2 | 1 | 2 | 9 | | |
| Cl$_2$CH—, NH$_2$, NH—CH$_2$—Ph | 4 | 9 | 9 | 9 | 9 | 9 | 9 | 9 | 9 | 8 | 9 | 9 | | | |
| | 1 | 9 | 9 | 9 | 9 | 9 | 9 | 8 | 9 | 8 | 9 | 9 | 9 | | |
| | .25 | 9 | 9 | 9 | 7 | 5 | 3 | 5 | 1 | 1 | 2 | 9 | 8 | | |
| | .06 | 9 | 9 | 9 | 0 | 0 | 0 | 1 | 0 | 0 | 0 | 0 | 0 | | |
| ClFCH—, NH$_2$, NH—cyclohexyl | 10 | 9 | 9 | 9 | 9 | 3 | 2 | 8 | 9 | 7 | | | | | |
| | 4 | 9 | 9 | 9 | 9 | 9 | 9 | 9 | 9 | 9 | 9 | 9 | 9 | | 3 |
| | 1 | 9 | 9 | 9 | 9 | 9 | 9 | 9 | 8 | 6 | 2 | 9 | 9 | | 1 |
| | 0.5 | 9 | 9 | 9 | 9 | 9 | 5 | 9 | 5 | 5 | 0 | 9 | 8 | | 1 |
| F$_2$ClC—, NH$_2$, NH—cyclohexyl | 10 | 9 | 9 | 9 | 9 | 9 | 7 | 8 | 9 | 9 | | | | | |
| | 1 | 9 | 9 | 9 | 9 | 9 | 9 | 9 | 9 | 8 | 9 | 9 | 9 | | 6 |
| | .25 | 9 | 9 | 9 | 9 | 9 | 9 | 9 | 9 | 5 | 9 | 9 | 9 | | 2 |
| | .13 | 9 | 9 | 5 | 5 | 9 | 9 | 9 | 9 | 2 | 5 | 9 | 9 | | 2 |
| Cl$_2$CH—, NH$_2$, NH—cyclohexyl | 10 | 9 | 9 | 9 | 9 | 9 | 6 | 6 | 9 | 5 | | | | | |
| | 4 | 9 | 9 | 9 | 9 | 9 | 9 | 9 | 9 | 9 | 9 | 9 | 9 | | 6 |
| | 0.5 | 9 | 9 | 9 | 8 | 9 | 7 | 7 | 8 | 3 | 5 | 9 | 8 | | 2 |
| | .13 | 9 | 7 | 5 | 0 | 9 | 5 | 3 | 7 | 0 | 0 | 0 | 7 | | 0 |
| F$_2$CH—, NH$_2$, NH—cyclohexyl | 10 | 9 | 9 | 9 | 9 | 8 | 9 | 9 | 9 | 7 | | | | | |
| | 1 | 9 | 9 | 9 | 9 | 9 | 9 | 9 | 9 | 9 | 9 | 9 | 9 | | 7 |
| | .25 | 9 | 9 | 9 | 9 | 9 | 7 | 7 | 8 | 5 | 9 | 9 | 9 | | 2 |
| | .06 | 9 | 7 | 9 | 7 | 9 | 7 | 5 | 3 | 0 | 0 | 9 | 7 | | 2 |
| F$_5$C$_2$—, NH$_2$, NH—cyclohexyl | 10 | 9 | 9 | 9 | 9 | 9 | 8 | 9 | 9 | 8 | | | | | |
| | 1 | 9 | 9 | 9 | 9 | 9 | 9 | 9 | 9 | 9 | 9 | 9 | 9 | | 6 |
| | .25 | 9 | 9 | 9 | 8 | 9 | 8 | 9 | 9 | 3 | 9 | 9 | 9 | | 5 |
| | .06 | 9 | 9 | 3 | 0 | 9 | 7 | 8 | 8 | 2 | 0 | 5 | 7 | | 3 |

TABLE III-continued

Postemergence Herbicidal Activity

| Structure | Treatment lb./Acre | Annual Weeds | | | | | | | | | Crops | | | | |
|---|---|---|---|---|---|---|---|---|---|---|---|---|---|---|---|
| | | LA | MU | PI | RAG | MG | BA | CR | GRF | WO | COR | COT | SOY | SB | RI |
| 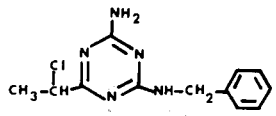 | 4 | 9 | 9 | 9 | 9 | 9 | 9 | 9 | 9 | 7 | 9 | 9 | 9 | | 3 |
| | 1 | 9 | 9 | 9 | 9 | 9 | 9 | 8 | 9 | 5 | 9 | 9 | 9 | | 3 |
| | .50 | 9 | 9 | 9 | 9 | 9 | 6 | 3 | 9 | 0 | 3 | 9 | 9 | | 3 |
| | .25 | 9 | 7 | 8 | 5 | 9 | 5 | 3 | 9 | 0 | 2 | 8 | 7 | | 0 |
| 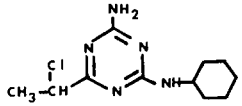 | 4 | 9 | 9 | 9 | 9 | 9 | 9 | 9 | 9 | 9 | 9 | 9 | 9 | | 5 |
| | 1 | 9 | 9 | 8 | 9 | 9 | 5 | 8 | 9 | 6 | 8 | 9 | 9 | | 3 |
| | .50 | 9 | 9 | 9 | 7 | 9 | 3 | 7 | 7 | 5 | 0 | 9 | 8 | | 1 |
| | .25 | 9 | 2 | 6 | 3 | 9 | 0 | 3 | 3 | 3 | 0 | 9 | 9 | | 1 |
| 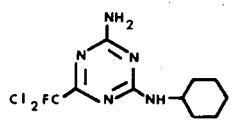 | 4 | 9 | 9 | 9 | 9 | 9 | 9 | 9 | 9 | 9 | 8 | 9 | 9 | | 8 |
| | 1 | 9 | 9 | 9 | 9 | 9 | 9 | 9 | 9 | 7 | 9 | 9 | 9 | | 7 |
| | .50 | 9 | 9 | 9 | 9 | 9 | 9 | 9 | 9 | 5 | 9 | 9 | 9 | | 6 |
| | .13 | 9 | 9 | 0 | 1 | 9 | 7 | 5 | 7 | 3 | 5 | 9 | 7 | | 2 |

EXAMPLE 6

The selective preemergence herbicidal activity of the compounds of the invention is exemplified by the following tests in which the seeds of a variety of monocotyledonous and dicotyledonous plants are separately mixed with potting soil and planted on top of approximately one inch of soil in 2 inch square plastic pots. After planting, the pots are sprayed with the selected aqueous acetone solution containing the test compound in sufficient quantity to provide the equivalent of about 0.25 to 10 pounds per acre of test compound per pot. The treated pots are then placed on greenhouse benches and cared for in accordance with greenhouse procedures. Three weeks after treatment, the tests are terminated and each pot is examined and rated according to the rating system set forth in the preceding example. The tabulated results of these tests establish the selective herbicidal proficiency of the test compounds, when properly applied, for controlling a variety of undesirable plant species. The specificity of the test compounds for control of undesirable weeds and grasses in the presence of corn, cotton, soybeans and rice is well demonstrated by these tests. Results are reported in the Table below.

TABLE IV

Preemergence Herbicidal Activity

| Structure | Treatment lb./Acre | Annual Weeds | | | | | | | | | Crops | | | | |
|---|---|---|---|---|---|---|---|---|---|---|---|---|---|---|---|
| | | LA | MU | PI | RAG | MG | BA | CR | GRF | WO | COR | COT | SOY | SB | RI |
| 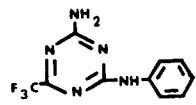 | 9 | 9 | 9 | 9 | 9 | | 7 | 7 | 9 | 9 | 0 | 0 | 2 | | 9 |
| | 3 | 9 | 9 | 9 | 7 | | 3 | 3 | 2 | 7 | 0 | 0 | 1 | | 9 |
| | 1 | 8 | 9 | 8 | 3 | | 1 | 1 | 1 | 1 | 0 | 0 | 0 | | 5 |
| | 0.5 | 8 | 7 | 8 | 0 | | 0 | 0 | 0 | 0 | 0 | 0 | 0 | | 3 |
| 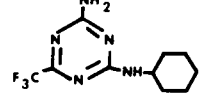 | 9 | 9 | 9 | 9 | 9 | | 9 | 9 | 9 | 9 | 2 | 9 | 9 | | 9 |
| | 3 | 9 | 9 | 9 | 9 | | 9 | 9 | 9 | 9 | 2 | 3 | 8 | | 9 |
| | 1 | 9 | 9 | 9 | 8 | | 9 | 7 | 8 | 8 | 1 | 0 | 6 | | 9 |
| | .13 | 9 | 9 | 7 | 0 | | 0 | 1 | 0 | 0 | 0 | 0 | 0 | | 9 |
| 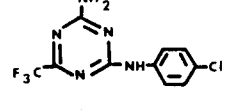 | 9 | 9 | 9 | 9 | 9 | | 1 | 7 | 7 | 1 | 0 | 0 | 3 | | 9 |
| | 3 | 9 | 9 | 9 | 9 | | 0 | 2 | 1 | 0 | 0 | 0 | 0 | | 9 |
| | 1 | 7 | 7 | 8 | 2 | | 0 | 0 | 0 | 0 | 0 | 0 | 0 | | 5 |
| | .5 | 5 | 0 | 2 | 0 | | 0 | 0 | 0 | 0 | 0 | 0 | 0 | | 0 |
| 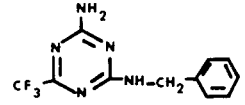 | 9 | 9 | 9 | 9 | 9 | | 9 | 9 | 9 | 9 | 9 | 9 | 9 | | 9 |
| | 3 | 9 | 9 | 9 | 9 | | 8 | 8 | 9 | 8 | 5 | 3 | 9 | | 9 |
| | 1 | 9 | 9 | 9 | 8 | | 5 | 9 | 6 | 8 | 1 | 1 | 1 | | 9 |
| | .25 | 9 | 9 | 9 | 3 | 1 | 7 | 6 | 0 | 1 | 0 | 0 | 0 | | |

TABLE IV-continued

| Structure | Treatment lb./Acre | Preemergence Herbicidal Activity Annual Weeds | | | | | | | | | Crops | | | | |
|---|---|---|---|---|---|---|---|---|---|---|---|---|---|---|---|
| | | LA | MU | PI | RAG | MG | BA | CR | GRF | WO | COR | COT | SOY | SB | RI |
| 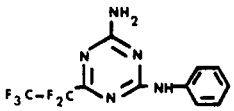 | 4<br>1 | 7<br>1 | 9<br>3 | 7<br>0 | 0<br>0 | | 0<br>0 | 2<br>0 | 0<br>0 | 0<br>0 | 0<br>0 | 0<br>0 | 0<br>0 | 7<br>2 | |
| 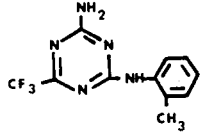 | 4<br>1<br>.5 | 8<br>6<br>3 | 8<br>5<br>1 | 8<br>1<br>0 | 8<br>2<br>0 | | 5<br>1<br>0 | 2<br>0<br>0 | 2<br>0<br>0 | 5<br>1<br>0 | 3<br>1<br>0 | 1<br>0<br>0 | 0<br>0<br>0 | 8<br>3<br>1 | |
| 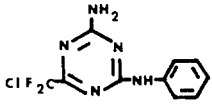 | 4<br>1 | 9<br>2 | 8<br>7 | 7<br>0 | 8<br>1 | | 1<br>0 | 2<br>0 | 0<br>0 | 0<br>0 | 0<br>0 | 0<br>0 | 0<br>0 | 7<br>7 | |
| 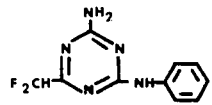 | 4 | 1 | 6 | 7 | 2 | | 2 | 2 | 1 | 1 | 1 | 0 | 0 | 6 | |
| 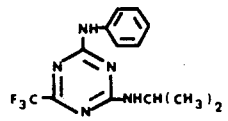 | 4 | 7 | 3 | 7 | 0 | | 0 | 1 | 1 | 0 | 0 | 0 | 0 | 0 | |
| 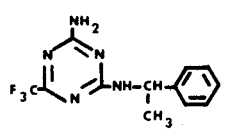 | 4<br>1<br>.5<br>.25 | 9<br>9<br>9<br>9 | 9<br>9<br>9<br>8 | 9<br>9<br>9<br>8 | 9<br>9<br>9<br>2 | | 8<br>7<br>2<br>0 | 9<br>8<br>7<br>1 | 9<br>7<br>1<br>0 | 9<br>7<br>1<br>1 | 2<br>1<br>1<br>0 | 2<br>1<br>1<br>0 | 9<br>9<br>0<br>0 | 9<br>9<br>9<br>8 | |
| 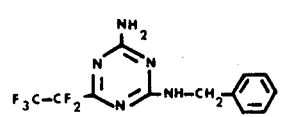 | 4<br>1<br>.5 | 9<br>9<br>9 | 9<br>9<br>9 | 9<br>9<br>0 | 9<br>0<br>0 | 5<br>1<br>0 | 9<br>0<br>0 | 9<br>2<br>0 | 9<br>0<br>0 | 1<br>0<br>0 | 0<br>0<br>0 | 1<br>0<br>0 | 2<br>0<br>0 | 1<br>0<br>0 | |
| 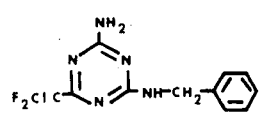 | 4<br>1<br>.5 | 9<br>9<br>9 | 9<br>9<br>9 | 9<br>9<br>9 | 9<br>9<br>0 | 9<br>0<br>0 | 9<br>8<br>0 | 9<br>8<br>2 | 9<br>3<br>0 | 1<br>0<br>0 | 0<br>0<br>0 | 5<br>0<br>0 | 3<br>2<br>0 | 2<br>0<br>0 | |
| 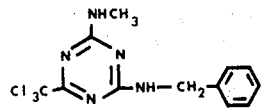 | 1 | 5 | 1 | 2 | 9 | 0 | 0 | 0 | 0 | 0 | 1 | 1 | 1 | 0 | |
| 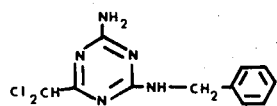 | 4 | 3 | 9 | 9 | 7 | 0 | 3 | 7 | 2 | 1 | 0 | 0 | 0 | 0 | |

TABLE IV-continued

| Structure | Treatment lb./Acre | Preemergence Herbicidal Activity Annual Weeds | | | | | | | | | Crops | | | | |
|---|---|---|---|---|---|---|---|---|---|---|---|---|---|---|---|
| | | LA | MU | PI | RAG | MG | BA | CR | GRF | WO | COR | COT | SOY | SB | RI |
| ClFCH-triazine-NH-cyclohexyl | 4 | 9 | 9 | 9 | 9 | 9 | 6 | 7 | 5 | 9 | 0 | 8 | 8 | | 0 |
| | 1 | 9 | 9 | 9 | 8 | 3 | 2 | 0 | 8 | 0 | 8 | 8 | | 0 |
| | .5 | 9 | 9 | 5 | 2 | 0 | 0 | 0 | 0 | 0 | 0 | 0 | 0 | | 0 |
| $F_2ClC$-triazine-NH-cyclohexyl | 4 | 9 | 9 | 9 | 8 | 9 | 9 | 9 | 9 | 9 | 0 | 9 | 9 | | 9 |
| | 1 | 9 | 9 | 9 | 3 | 8 | 9 | 7 | 7 | 6 | 0 | 3 | 9 | | 5 |
| | .5 | 9 | 9 | 5 | 0 | 5 | 8 | 6 | 5 | 3 | 0 | 0 | 3 | | 2 |
| | .25 | 9 | 9 | 0 | 0 | 2 | 2 | 2 | 0 | 0 | 0 | 0 | 3 | | 0 |
| $Cl_2CH$-triazine-NH-cyclohexyl | 4 | 9 | 9 | 9 | 3 | 7 | 5 | 8 | 5 | 2 | 0 | 3 | 7 | | 3 |
| | 1 | 9 | 9 | 0 | 3 | 2 | 3 | 3 | 2 | 0 | 0 | 0 | 7 | | 0 |
| | .5 | 9 | 9 | 0 | 0 | 0 | 0 | 3 | 0 | 0 | 0 | 0 | 0 | | 0 |
| $F_2CH$-triazine-NH-cyclohexyl | 4 | 9 | 9 | 9 | 9 | 9 | 9 | 9 | 9 | 9 | 6 | 9 | 9 | | 9 |
| | 1 | 9 | 9 | 9 | 9 | 9 | 9 | 9 | 9 | 9 | 2 | 9 | 9 | | 9 |
| | .5 | 9 | 9 | 9 | 8 | 9 | 9 | 9 | 8 | 8 | 0 | 8 | 8 | | 5 |
| | .25 | 8 | 9 | 9 | 8 | 7 | 8 | 8 | 5 | 5 | 0 | 1 | 7 | | 5 |
| $F_5C_2$-triazine-NH-cyclohexyl | 4 | 9 | 9 | 9 | 3 | 9 | 9 | 9 | 9 | 6 | 0 | 5 | 8 | | 2 |
| | 1 | 9 | 9 | 9 | 0 | 9 | 8 | 8 | 3 | 0 | 0 | 0 | 3 | | 0 |
| | .5 | 9 | 9 | 7 | 0 | 9 | 3 | 7 | 3 | 0 | 0 | 0 | 3 | | 0 |
| | .25 | 9 | 9 | 0 | 0 | 0 | 0 | 5 | 0 | 0 | 0 | 0 | 2 | | 0 |
| $CH_3$-CHCl-triazine-NH-$CH_2$-phenyl | 4 | 2 | 9 | 8 | 0 | 0 | 0 | 0 | 2 | 0 | 0 | 0 | 0 | | 0 |
| $CH_3$-CHCl-triazine-NH-cyclohexyl | 4 | 9 | 9 | 9 | 7 | 8 | 5 | 9 | 8 | 7 | 2 | 6 | 8 | | 5 |
| | 1 | 9 | 8 | 3 | 3 | 0 | 2 | 5 | 3 | 3 | 2 | 2 | 5 | | 3 |
| | .5 | 8 | 7 | 0 | 3 | 0 | 0 | 0 | 3 | 3 | 0 | 0 | 2 | | 2 |
| $Cl_2FC$-triazine-NH-cyclohexyl | 10 | 9 | 9 | 9 | 0 | 8 | 7 | 8 | 9 | 3 | | | | | |
| | 4 | 9 | 9 | 6 | 6 | 9 | 8 | 9 | 9 | 1 | 0 | 7 | 7 | | 0 |
| | 1 | 9 | 9 | 0 | 0 | 2 | 3 | 6 | 0 | 0 | 0 | 0 | 0 | | 0 |

We claim:

1. A method for the control of undesirable plant species comprising, contacting the undesirable plant species or soil containing seeds of undesirable plant species with a herbicidally effective amount of a compound of the formula:

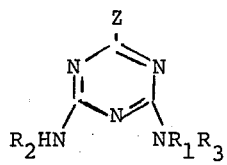

where Z is haloalkyl $C_1$–$C_3$ or haloalkenyl $C_1$–$C_3$ containing from 1 to 5 halogen atoms; $R_1$ and $R_2$ each represent hydrogen, alkyl $C_1$–$C_4$ or cyanoalkyl wherein the alkyl group contains 1 to 4 carbon atoms; $R_3$ is phenyl, chlorophenyl, methylphenyl, cyclohexyl, methylcyclohexyl, benzyl or 2-methylbenzyl.

2. A method according to claim 1 for the postemergence control of undesirable plant species wherein the herbicidally active compound is applied to the foliage of the undesirable plant species at a rate sufficient to provide from about 0.06 to 10 pounds of active compound per acre.

3. A method according to claim 1 for the selective preemergence control of undesirable plant species wherein the herbicidally active compound is applied to soil containing seeds of the undesirable plant species to provide from about 0.06 to 10 pounds of active compound per acre.

4. A method according to claim 1 wherein the compound is 2-amino-4-cyclohexylamino-6-(difluoromethyl)-s-triazine.

5. A method according to claim 1 wherein the compound is 2-amino-4-cyclohexylamino-6-(trifluoromethyl)-s-triazine.

6. A method according to claim 1 wherein the compound is 2-amino-4-benzylamino-6-(chlorodifluoromethyl)-s-triazine.

7. A method according to claim 1 wherein the compound is 2-amino-4-cyclohexylamino-6-(pentafluoroethyl)-s-triazine.

8. A method according to claim 1 wherein the compound is 2-amino-4-cyclohexylamino-6-(chlorodifluoromethyl)-s-triazine.

9. A method according to claim 1 wherein the compound is 2-amino-4-benzylamino-6-(trifluoromethyl)-s-triazine.

* * * * *